United States Patent [19]

Förg et al.

[11] Patent Number: 5,414,190

[45] Date of Patent: May 9, 1995

[54] PROCESS TO RECOVER LIQUID METHANE

[75] Inventors: Wolfgang Förg, Icking; Rudolf Stockman, Buchloe, both of Germany

[73] Assignee: Linde Aktiengesellschaft, Wiesbaden, Germany

[21] Appl. No.: 148,229

[22] Filed: Nov. 8, 1993

[30] Foreign Application Priority Data

Nov. 6, 1992 [DE] Germany .................. 42 37 620.3

[51] Int. Cl.$^6$ .................. C07C 7/00; F25J 3/02
[52] U.S. Cl. .................. 585/802; 62/24; 95/50; 95/121
[58] Field of Search .................. 585/802; 62/24; 95/50, 95/121

[56] References Cited

U.S. PATENT DOCUMENTS 4,681,612  7/1987  O'Brien et al. .................. 62/23
4,936,887  6/1990  Waldo et al. .................. 62/24
5,233,837  8/1993  Callahan .................. 62/38

*Primary Examiner*—Asok Pal
*Assistant Examiner*—Nhat D. Phan
*Attorney, Agent, or Firm*—Millen, White, Zelano, & Branigan

[57] ABSTRACT

To recover liquid methane from a feed gas mixture (1) essentially consisting of methane, $C_{2+}$ hydrocarbons, carbon dioxide and nitrogen, the feed gas mixture (1) is fed first to an adsorption unit (E) and freed from water; dried feed gas mixture (2) is fed to a membrane separating unit (F), wherein the carbon dioxide is separated down to a residual content less than 2% by volume (9) and resultant gas mixture (3) now essentially consisting of methane, $C_{2+}$ hydrocarbons and nitrogen is fed to a low-temperature distillation (A) wherein the $C_{2+}$ hydrocarbons as well as the residual content of carbon dioxide are separated by distillation.

11 Claims, 3 Drawing Sheets

PROCESS TO RECOVER LIQUID METHANE

BACKGROUND OF THE INVENTION

The invention relates to a process to recover liquid methane from a feed gas mixture comprising essentially methane, $C_{2+}$ hydrocarbons, carbon dioxide and nitrogen.

Highly pure liquid methane is used to an increasing extent as a non-polluting fuel for diesel engines in locomotives, buses and trucks. The liquid methane is generally recovered from natural gas. For example, in U.S. Pat. No. 4,761,167, a process to recover methane from a gas mixture containing methane, $C_{2+}$ hydrocarbons, carbon dioxide and nitrogen provides feeding the gas mixture first to a cryogenic distillation stage, in which the $C_{2+}$ hydrocarbon fraction as well as a first carbon dioxide fraction are recovered. The remaining $CH_4/N_2/CO_2$ gas mixture is then conveyed to a pressure swing adsorption stage where the mixture is freed from carbon dioxide. In a nitrogen separating unit downstream of the pressure swing adsorption stage, the resultant gas mixture is separated to provide the methane product fraction as well as a nitrogen fraction, and the latter is used to regenerate the adsorber loaded with carbon dioxide. This process is particularly useful if the nitrogen concentration in the feed gas mixture is approximately of the same order of magnitude as the methane concentration.

In an alternative to this process, there is employed, instead of the cryogenic distillation stage, an amine scrubbing stage to separate the carbon dioxide from the feed gas mixture. In this case, is necessary to employ a downstream adsorption unit for drying the resultant water-saturated feed gas mixture from the amine washing stage. This procedure has the drawback, however, that the adsorption unit, because of the complete water saturation of the gas stream exiting from the amine washing stage, must be very large. Furthermore, the system must provide for the disposal or recycling of the amine scrubbing agent used in the carbon dioxide separation stage.

SUMMARY OF THE INVENTION

An object of one aspect of this invention is to provide a process to recover liquid methane, in which, on the one hand, an amine washing stage can be avoided, and, on the other hand, an adsorption unit can be used which is smaller in comparison with prior art processes.

Upon further study of the specification and appended claims, further objects and advantages of this invention will become apparent to those skilled in the art.

To achieve this object according to the invention, a process is provided wherein:

a) the feed gas mixture is fed first to an adsorption unit and freed from water in the latter;
b) the dried feed gas mixture is fed to a membrane separation stage where the carbon dioxide is separated down to a content lower than 2% by volume; and
c) the gas mixture now essentially consisting of methane, $C_{2+}$ hydrocarbons and nitrogen is fed to a low-temperature distillation stage wherein the $C_{2+}$ hydrocarbons as well as the residual content of carbon dioxide are separated by distillation.

If desired, the resultant purified methane can be liquefied by an external refrigeration cycle and an expansion step. The resultant liquid methane is then transferred to a storage tank. By virtue of boil-off from the storage tank, the liquid is gradually depleted in residual nitrogen, as one method of removing the nitrogen.

The combination according to the invention of adsorption to dry the feed gas stream, membrane separation to remove carbon dioxide, and low-temperature distillation to recover the liquid methane product stream results in a process that is very easy to operate, quick to start and economical. In addition to the water contained in the feed gas mixture, any glycol in the feed gas can also be removed by the adsorption stage. Adsorption processes to dry all types of gas streams are well known from the literature. Adsorption agents for the drying step of this invention include but are not limited to silica gel, activated alumina and molecular sieve (zeolite).

In the membrane separation stage, a reduction of the carbon dioxide content to less than 2% by volume, generally about 0.5 to 1.8% by volume, can be achieved with the selection of suitable membranes in one, two or more separation stages, for example, a spiral wound membrane manufactured by Grace Membrane Systems from cellulosic acetate, described in Chemical Engineering Progress, January 1989, pages 41–62, Economics of Gas Separation Membranes.

In the liquefaction occurring in the downstream low-temperature distillation stage, the residual carbon dioxide together with the $C_{2+}$ hydrocarbons is removed down to a concentration of less than 50 ppm with very little additional expenditure over that generally required for the liquefaction of the methane. Moreover, this minor additional expenditure is also offset, in that the gas stream exiting from the membrane separation unit enters the low-temperature distillation stage at about 300K. In contrast, in the case of an amine scrubbing stage upstream of the low-temperature distillation stage, the temperature of the exit gas was approximately 322K. This 22° difference again would, of course, entail an additional expenditure of energy for the liquefaction of the resultant gas within the low-temperature distillation stage.

In the process according to the invention, additional preferred features are optionally employed. In one, the carbon dioxide fraction recovered in the membrane separation stage is mixed together with the $C_{2+}$ hydrocarbon fraction from the low-temperature distillation stage as well as with the boil-off gas from a liquid methane storage tank downstream of the process, and the resultant mixture is fed to the adsorption unit as regenerating gas.

In a further development of the invention, it is proposed to compress in one stage or in multiple stages the carbon dioxide fraction, recovered in the membrane separating unit, together with the boil-off gas before mixing with the $C_{2+}$ hydrocarbon fraction.

In another advantageous embodiment of the process, in the low-temperature distillation, a column is provided to separate a liquid cut of $C_{2+}$ hydrocarbons and the residual carbon dioxide. This liquid cut is vaporized by indirect heat exchange with the gas mixture from the membrane separation stage, said gas mixture essentially consisting of methane, $C_{2+}$ hydrocarbons and nitrogen, and having been previously cooled by a partial stream of a refrigeration cycle medium used for the low-temperature distillation stage.

BRIEF DESCRIPTION OF THE DRAWINGS

Various other objects, features and attendant advantages of the present invention will be more fully appreciated as the same becomes better understood when considered in conjunction with the accompanying drawings, in which like reference characters designate the same or similar parts throughout the several views, and wherein.

DETAILED DESCRIPTION OF THE DRAWINGS

Figure 1:
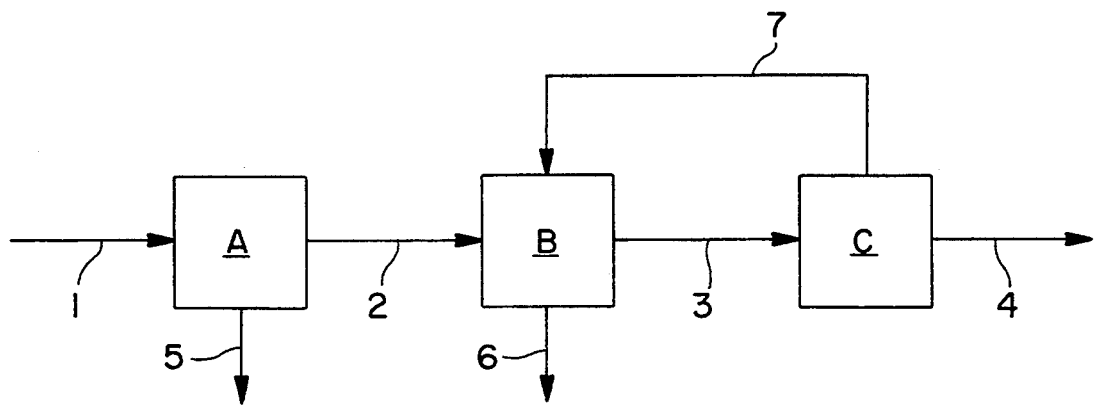
FIG. 1 is a box flowsheet of the process of U.S. Pat. No. 4,761,167.

FIG. 1 represents a process as it is described in U.S. Pat. No. 4,761,167. In this case, the feed gas stream is fed to cryogenic distillation stage A by pipe 1 and in the distillation, the $C_{2+}$ hydrocarbons as well as a first carbon dioxide stream are recovered by pipe 5. A $CH_4/N_2/CO_2$ gas mixture is fed to pressure swing adsorption stage B by pipe 2. In it, an adsorptive separation of this gas mixture provides a $CO_2$-rich fraction, discharged by pipe 6, and a $CH_4/N_2$-rich fraction, which is fed by pipe 3 to nitrogen separation unit C. While the methane product stream is recovered by pipe 4, the nitrogen fraction is recycled by pipe 7 to pressure swing adsorption stage B and used therein as regenerating gas for the adsorbers loaded with carbon dioxide.

Figure 2:
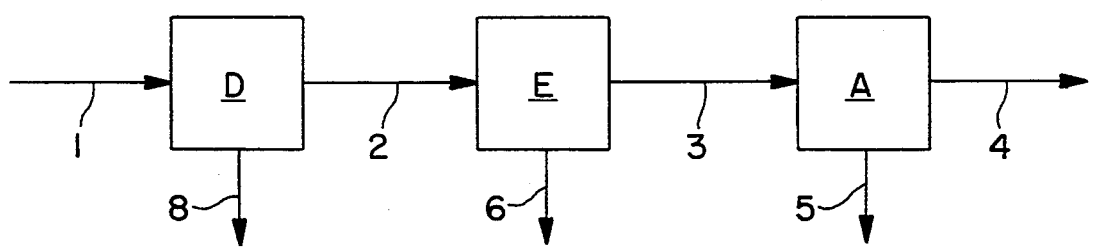
FIG. 2 is a box flowsheet of a prior art process employing an amine scrubbing stage.

FIG. 2 shows a combination of an amine scrubbing D to remove the carbon dioxide, an adsorption unit E to dry the resultant $CO_2$ depleted feed gas mixture and a cryogenic distillation A to separate the $Ca_{2+}$ hydrocarbons. The carbon dioxide separated in the amine scrubbing stage D is discharged by pipe 8, the water recovered in adsorption unit E by pipe 6 and the $C_{2+}$ fraction separated in cryogenic distillation A by pipe 5.

Figure 3:
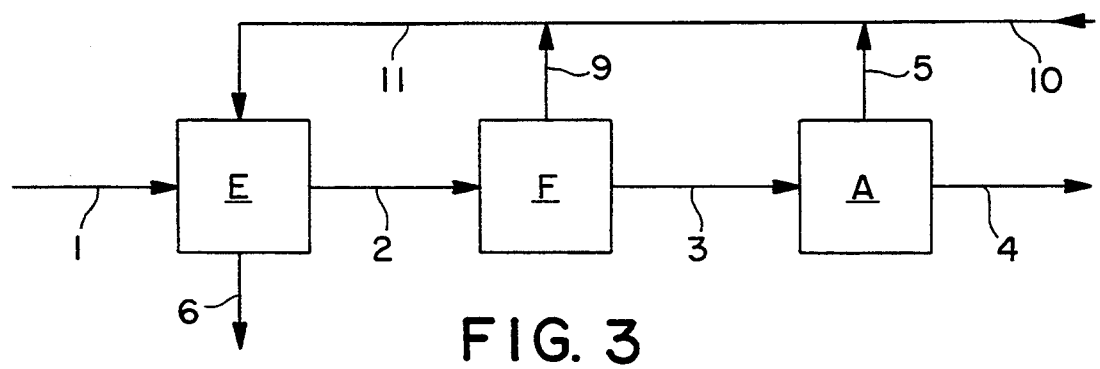
FIG. 3 is a box flowsheet of the invention.

FIG. 3 shows the process according to the invention, comprising an adsorption unit E to dry the feed gas mixture, a membrane separation unit F to separate carbon dioxide as well as a low-temperature distillation stage A to separate the dried gas stream, partially freed from carbon dioxide, into a liquid methane product fraction, which is discharged by pipe 4, as well as in a $C_{2+}$- and $CO_2$-containing fraction, which is given off by pipe 5. The carbon dioxide fraction drawn off from membrane separation unit F by pipe 9, together with the $C_{2+}$- and $CO_2$-rich fraction drawn off from low-temperature distillation A by pipe 5 and a boil-off gas brought in by pipe 10, which comes from a methane tank downstream to this process, can be fed by pipe 11 to adsorption unit E as regenerating gas to regenerate the adsorber loaded with $H_2O$. As the adsorption material in stage E, it is preferred to employ molecular sieve (zeolite). As the membrane material in stage F, it is preferred to employ cellulosic acetate or a composite material (dimethylsilicone and polyester). Nitrogen in the methane can be removed in the boil-off gas or by intermediate flashing to a gas/liquid separator or by a stripping column.

Figure 4:
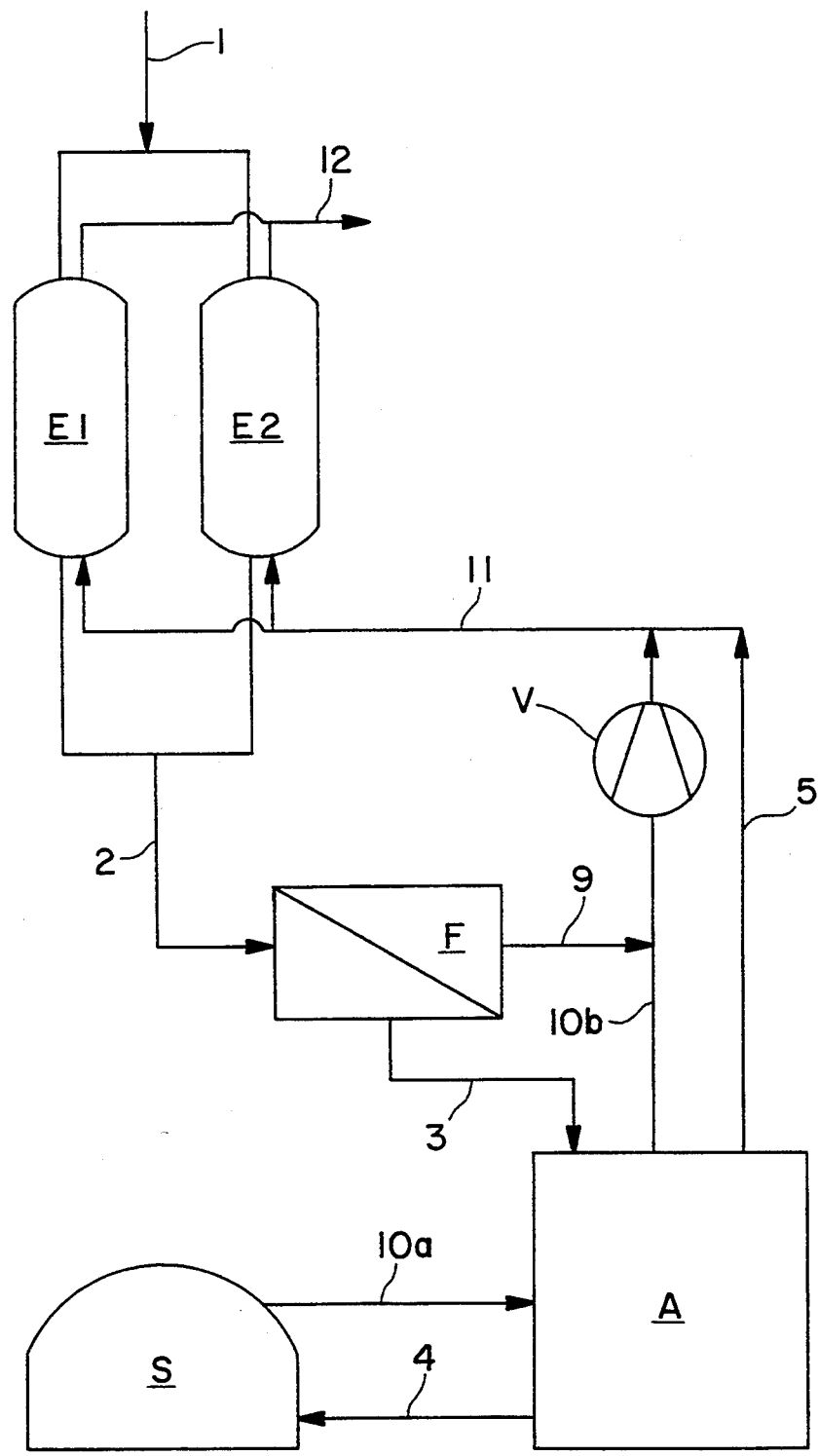
FIG. 4 is a comprehensive schematic flowsheet of the invention wherein two interchangeable adsorbers are employed and certain gas streams are recycled to the adsorbers for regeneration purposes.

FIG. 4 shows an embodiment of the process according to the invention analogous to FIG. 3. The drying of the feed gas mixture from pipe 1 takes place in this case in an adsorption unit comprising at least two adsorbers E1 and E2. The dried feed gas mixture is fed by pipe 2 to a membrane separation unit F, wherein carbon dioxide is separated and withdrawn by pipe 9. The resultant gas mixture now essentially consisting of methane, $C_{2+}$ hydrocarbons and nitrogen is fed by pipe 3 to a low-temperature unit A wherein the $C_{2+}$ hydrocarbons as well as the residual carbon dioxide are separated by distillation and removed by pipe 5 and the nitrogen is removed by expansion. The highly pure liquid methane product stream recovered in the low-temperature distillation stage is conveyed by pipe 4 to liquid methane storage tank S. The boil-off gas escaping from liquid methane storage tank S is recycled by pipe 10a to the low-temperature unit A, warmed thereon to transfer the refrigeration values and then fed by pipe 10b to compressor V, after being admixed with the $CO_2$-rich process stream in pipe 9 from the membrane separation unit, After compression, this process stream is mixed with the $C_2$-rich fraction in pipe 5 and fed to adsorbers E1 and E2 by pipe 11 as regenerating gas. The regenerating gas loaded with water is discharged from the unit by pipe 12.

Figure 5:
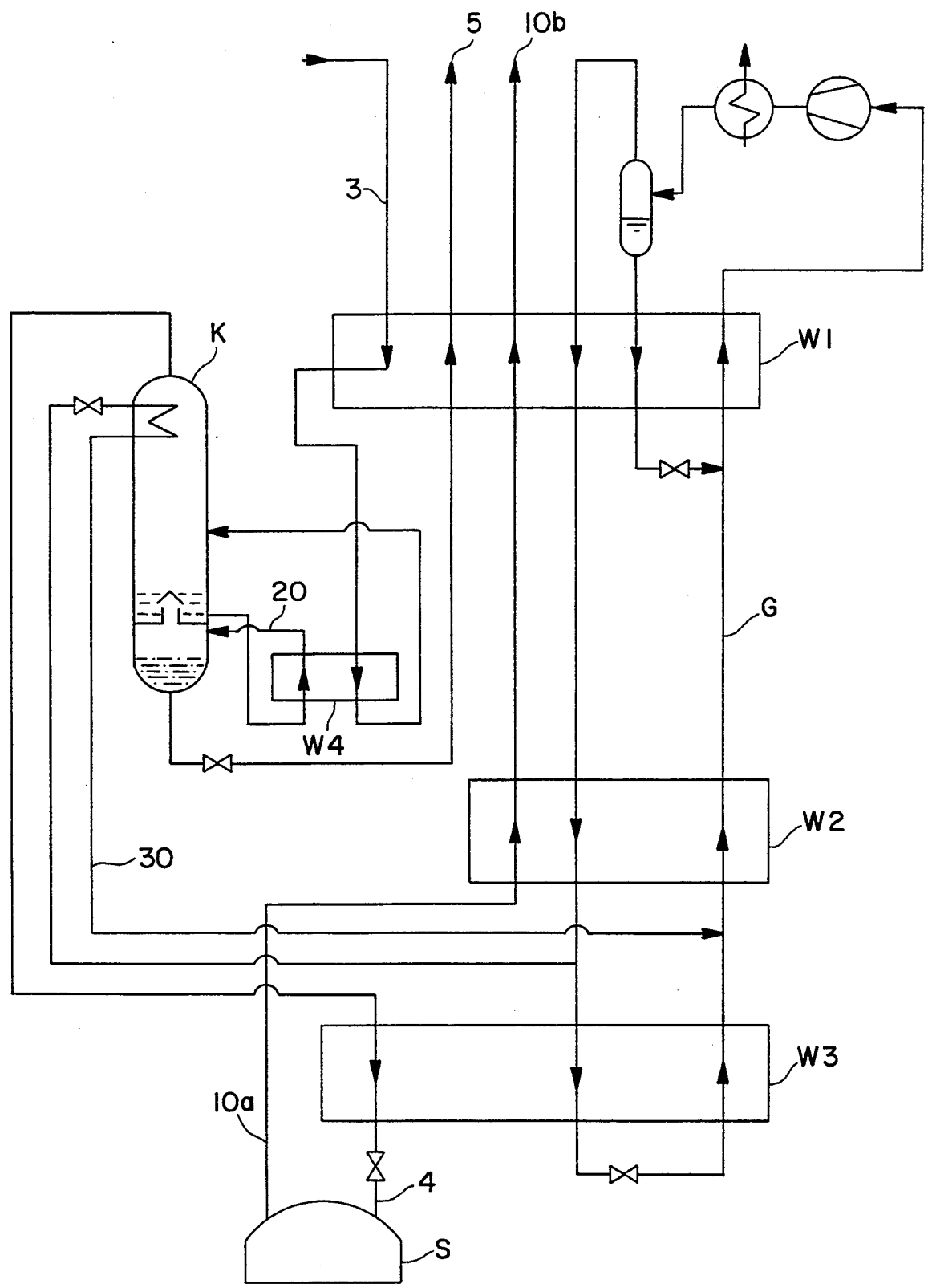
FIG. 5 is a schematic comprehensive flowsheet of the low temperature distillation stage of FIG. 4 with ancillary equipment.

FIG. 5 shows a detailed embodiment of the low-temperature distillation stage of FIG. 4. A conventional refrigerant mixture cycle G is used to provide the needed process refrigeration. The process stream conveyed from membrane separating unit F (FIG. 3) by pipe 3 to the low-temperature distillation is first cooled in heat exchanger W1 countercurrently to the process streams to be heated. Before being fed to column K, the resultant cooled process stream from the membrane separation unit is further cooled in heat exchanger W4 by a $C_2$-rich liquid stream drawn off from column K by pipe 20, which in turn is vaporized and is recycled into column K below the plate holding said liquid stream. The head of column K is cooled by a partial stream drawn off in pipe 30 from refrigerant mixture cycle G. At the bottom of column K, a $C_{2+}$ hydrocarbon fraction, in which the residual carbon dioxide is contained, is drawn off by pipe 5, heated in heat exchanger W1 and then is discharged from the low-temperature stage. At the head of column K, a purified methane fraction is recovered, liquefied in heat exchanger W3 and conveyed by pipe 4 to liquid methane storage tank S. The boil-off gas exiting from this liquid methane storage tank S is conveyed by pipe 10a back to the low-temperature unit, heated in the latter in heat exchangers W2 and W1 and is then removed by pipe 10b from the low-temperature unit.

Table 1 contains an exemplified material balance relating to the process represented in FIGS. 4 and 5. In this case, the material balance data are calculated at the points in the process piping to which the respective reference numbers pertain.

The invention is particularly applicable to the recovery of liquid methane from feed gases of the following composition:

|  | % by volume S.T.P. |
|---|---|
| $CH_4$ | 50–97 |
| $C_{2+}$ | 1–15 |

-continued

| | % by volume S.T.P. |
|---|---|
| $CO_2$ | 2-15 |
| $N_2$ | 0-15 |
| $H_2O$ | saturated |

This invention is applicable to the production of highly pure liquid methane which is defined herein as greater than 99% by volume, preferably grater than 99.5% by volume.

TABLE 1

| PIPE | 1 | 2 | 3 | 4 | S | 10a | 10b | 5 | 9 | 11 |
|---|---|---|---|---|---|---|---|---|---|---|
| $N_2$ [Mol-%] | 0,75 | 0,75 | 0,77 | 0,88 | 0,31 | 8,13 | 8,13 | 0,00 | 0,53 | 1,99 |
| $CH_4$ [Mol-%] | 88,75 | 88,77 | 90,28 | 99,12 | 99,69 | 91,87 | 91,87 | 29,97 | 71,85 | 57,25 |
| $C_{2+}$ [Mol-%] | 6,56 | 6,55 | 6,95 | 0,00 | 0,00 | 0,00 | 0,00 | 54,41 | 2,25 | 25,48 |
| $CO_2$ [Mol-%] | 3,92 | 3,93 | 2,00 | 0,00 | 0,00 | 0,00 | 0,00 | 15,62 | 25,37 | 15,22 |
| $H_2O$ [Mol-%] | 0,02 | 0,00 | 0,00 | 0,00 | 0,00 | 0,00 | 0,00 | 0,00 | 0,00 | 0,06 |
| T [K] | 300,0 | 300,0 | 300,0 | 119,3 | 111,7 | 144,3 | 305,0 | 305,0 | 300,0 | 307,0 |
| p [bar] | 35,0 | 34,0 | 33,5 | 32,1 | 1,1 | 1,1 | 1,1 | 13,0 | 1,1 | 11,4 |

In all instances, commas should be replaced with decimal points.

The entire disclosures of all applications, patents, and publications, cited above, and of corresponding German Application P 42 37 620.3, filed Nov. 6, 1992, are hereby incorporated by reference.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A process to recover methane from a feed gas mixture of methane, $C_{2+}$ hydrocarbons, carbon dioxide, nitrogen and $H_2O$, said process comprising:
    a) introducing the feed gas mixture to a regenerable adsorption stage (E) to selectively remove water therefrom;
    b) passing the resultant dried feed gas mixture to a membrane separating stage (F) to selectively remove the carbon dioxide down to a residual content less than 2% by volume (9); and
    c) passing the resultant gas mixture of methane, $C_{2+}$ hydrocarbons and nitrogen to a distillation stage (A) to separate the $C_{2+}$ hydrocarbons and the residual content of carbon dioxide from the methane.

2. A process according to claim 1 further comprising liquefying the resultant methane from the distillation stage, passing the liquefied methane to a liquid methane storage tank, and withdrawing boil-off gas from said storage tank, thereby gradually reducing the relative content of nitrogen in the liquefied methane.

3. A process according to claim 2 further comprising withdrawing carbon dioxide removed from the membrane separating stage and mixing said carbon dioxide together with the separated $C_{2+}$ hydrocarbon fraction from the distillation stage and the boil-off gas from the liquid methane storage tank and passing the resultant mixture to the adsorption stage and employing said mixture as a regenerating gas to regenerate the adsorption stage.

4. A process according to claim 3, wherein the carbon dioxide recovered from the membrane separation stage, together with the boil-off gas is compressed before being mixed with the $C_{2+}$ hydrocarbon fraction.

5. A process according to claim 2, wherein the membrane separation stage comprises at least two membrane separation units.

6. A process according to claim 1, wherein the adsorption stage comprises at least two interchangeable adsorbers.

7. A process according to claim 5, wherein the adsorption stage comprises at least two interchangeable adsorbers.

8. A process according to claim 1, said distillation stage comprising a refrigeration cycle and a column to separate the $C_{2+}$ hydrocarbons and the residual carbon dioxide, and wherein the separated $C_{2+}$ hydrocarbons and the residual carbon dioxide are passed in indirect heat exchange relationship to the gas mixture from the membrane separation unit, said gas mixture consisting essentially of methane, $C_{2+}$ hydrocarbons and nitrogen.

9. A process according to claim 3, said distillation stage comprising a refrigeration cycle and a column to separate the $C_{2+}$ hydrocarbons and the residual carbon dioxide, and wherein the separated $C_{2+}$ hydrocarbons and the residual carbon dioxide are passed in indirect heat exchange relationship to the gas mixture from the membrane separation unit, said gas mixture consisting essentially of methane, $C_{2+}$ hydrocarbons and nitrogen.

10. A process according to claim 8, wherein said gas mixture is previously cooled by said refrigeration cycle prior to said indirect heat exchange.

11. A process according to claim 9, wherein said gas mixture is previously cooled by said refrigeration cycle prior to said indirect heat exchange.

* * * * *